US011804205B2

(12) United States Patent
Van 'T Hof et al.

(10) Patent No.: US 11,804,205 B2
(45) Date of Patent: Oct. 31, 2023

(54) ACOUSTIC FILTER AND METHOD OF MANUFACTURING

(71) Applicant: Dynamic Ear Company B.V., Delft (NL)

(72) Inventors: Pieter Gerard Van 'T Hof, Delft (NL); Engbert Wilmink, Delft (NL)

(73) Assignee: SONOVA AG, Staefa (CH)

( * ) Notice: Subject to any disclaimer, the term of this patent is extended or adjusted under 35 U.S.C. 154(b) by 1510 days.

(21) Appl. No.: 15/781,510

(22) PCT Filed: Dec. 9, 2016

(86) PCT No.: PCT/NL2016/050862
§ 371 (c)(1),
(2) Date: Jun. 5, 2018

(87) PCT Pub. No.: WO2017/099600
PCT Pub. Date: Jun. 15, 2017

(65) Prior Publication Data
US 2018/0277087 A1    Sep. 27, 2018

(30) Foreign Application Priority Data

Dec. 11, 2015    (NL) .................................... 2015947

(51) Int. Cl.
*B29C 45/34*    (2006.01)
*G10K 11/162*    (2006.01)
(Continued)

(52) U.S. Cl.
CPC ............ *G10K 11/162* (2013.01); *A61F 11/08* (2013.01); *B29C 45/0046* (2013.01);
(Continued)

(58) Field of Classification Search
CPC ..... B29C 45/235; B29C 45/34; A61F 11/085; A61F 11/08
See application file for complete search history.

(56) References Cited

U.S. PATENT DOCUMENTS 4,353,364 A    10/1982    Woods
6,671,381 B1    12/2003    Lux-Wellenhof
(Continued)

FOREIGN PATENT DOCUMENTS

EP    1046382 A1    10/2000
JP    S51-115816 A    10/1976
(Continued)

OTHER PUBLICATIONS

International Search Report PCT/NL2016/050862 dated Mar. 28, 2017.

*Primary Examiner* — Alison L Hindenlang
*Assistant Examiner* — Debjani Roy
(74) *Attorney, Agent, or Firm* — Pillsbury Winthrop Shaw Pittman, LLP

(57) ABSTRACT

An injection moulded acoustic filter comprising a foil piece or filter structure having a plurality of micro-slits configured to act as acoustic channels through the foil piece for filtering sound waves impinging the foil piece. The micro-slits have a maximum slit width across a surface of the foil piece of less than one hundred micrometres and a combined slit length along the surface of the foil piece of at least five millimetres. An earplug comprising the acoustic filter. A method and mould for manufacturing the acoustic filter.

15 Claims, 10 Drawing Sheets

(51) Int. Cl.
    *A61F 11/08*         (2006.01)
    *B29C 45/00*        (2006.01)
    *B29C 45/26*        (2006.01)
    *B29L 31/00*         (2006.01)

(52) U.S. Cl.
    CPC ............ *B29C 45/263* (2013.01); *B29C 45/34* (2013.01); *A61F 11/085* (2022.01); *A61F 2240/001* (2013.01); *B29K 2995/0002* (2013.01); *B29K 2995/0093* (2013.01); *B29L 2031/768* (2013.01)

(56) References Cited

U.S. PATENT DOCUMENTS

| | | | | |
|---|---|---|---|---|
| 2002/0179365 A1* | 12/2002 | Meussen | ................. | A61F 11/08 |
| | | | | 181/135 |
| 2003/0159878 A1* | 8/2003 | Hakansson | ............. | A61F 11/08 |
| | | | | 181/135 |
| 2008/0095393 A1* | 4/2008 | Klein | ................... | H04R 1/1016 |
| | | | | 381/380 |
| 2019/0321320 A1* | 10/2019 | Amminger | ........... | A61K 31/202 |

FOREIGN PATENT DOCUMENTS

| | | |
|---|---|---|
| WO | 01/76520 A1 | 10/2001 |
| WO | 2006/056913 A1 | 6/2006 |

\* cited by examiner

ACOUSTIC FILTER AND METHOD OF MANUFACTURING

CROSS-REFERENCE TO RELATED APPLICATIONS

This is the U.S. National Stage of PCT/NL2016/050862, filed Dec. 9, 2016, which in turn claims priority to: Netherlands Application No. 2015947, filed Dec. 11, 2015, the contents of each of these applications being incorporated herein by reference in their entireties.

TECHNICAL FIELD AND BACKGROUND

The present disclosure relates to an acoustic filter, an earplug comprising the acoustic filter, and a method of manufacturing the acoustic filter.

Acoustic filtering can be realised by blocking part of a canal and only allowing sound to enter through one or more openings having restricted dimensions. Without being bound by theory, it is found that the acoustic properties of openings can be described by parameters such as the acoustic mass and the acoustic resistance. For example the acoustic resistance $R_a$ of a circular opening with a radius of a can be calculated as follows with $\eta$ the viscosity of air and L, the depth of the opening in the sound traveling direction:

$$R_a = \frac{8\eta L}{\pi a^4}$$

Furthermore, the acoustic mass $m_a$ of the circular opening can be calculated as follows with $\rho$ the density of air:

$$m_a = \frac{4\rho L}{3\pi a^2}$$

The above formulas combined give the ratio of the acoustic mass $m_a$ over the acoustic resistance $R_a$:

$$\frac{m_a}{R_a} = \frac{\rho}{6\eta}a^2$$

The inventors find that this ratio may be used to qualify the acoustic performance of a sound filter. For example, it is typically desired to have an acoustic transfer function that has a minimally varying attenuation over the frequency range of speech in a range between about hundred and four thousand Hertz. However, when using openings as described above, the attenuation is found to be higher for higher frequencies particularly if the acoustic mass term is relatively high compared to the resistive term. Hence it is desired to make the ratio as low as possible. In view of the formulas above, this may be accomplished by having the radius a of the openings relatively small. From the considerations above, it is clear that for most acoustic applications, it would be preferred to use a mesh with many small openings rather than a single hole, since the mesh may provide a more natural (flat) response, i.e. less frequency dependence of the attenuation.

For example, precision woven meshes for use in acoustic applications can be made of a specific pattern made from two or more layers of wires woven together. To manufacture an acoustic filter, a small piece of mesh is typically cut from a larger screen of mesh in the required dimensions. This can be done by punching, cutting, and laser cutting or similar. However, since the mesh is generally made of strong nylon, metal or PET, punching or cutting is tough and tools may deteriorate soon. After providing the mesh in the desired dimensions, it is typically connected to a carrier part to give it support for mounting onto another part or for separate use. For example a connection between the mesh and the carrier may comprise gluing, ultrasonic welding or injection moulding the part around the mesh. The latter two options are found to provide relatively clean result, however at relatively high manufacturing cost Accordingly, it is desired to provide an acoustic filter having similar acoustic performance as a mesh at decreased manufacturing cost.

SUMMARY

These or other desires may be achieved by aspects of the present disclosure wherein an injection moulded acoustic filter is provided. The acoustic filter comprises a relatively thin piece of material referred herein as foil piece. The foil piece has one or more openings through the foil piece. The openings are configured to act as (the only) acoustic channels through the foil piece for filtering sound waves impinging the foil piece. The openings have a smallest width dimension that is relatively small, e.g. less than two hundred micrometres, less than one hundred micrometres, or even less than fifty micrometres. Advantageously, the openings comprise a plurality of micro-slits. Accordingly, a maximum slit width may define the aforementioned smallest width of the openings. On the one hand, a width dimension of the slits is relatively small. The thinner the slit, the more restricted the sound passage. On the other hand, a length dimension of the slits can be relatively large. For example, a combined length of the one or more micro-slits is preferably at least five millimetre, at least ten millimetre, at least twenty millimetre, or even more than forty millimetre. The longer the length, the more total open area for passing sound through the filter.

The inventors find that such micro-slits can provide similar acoustic behaviour as the small holes in a mesh. Without being bound by theory it is considered that the width of the slit may play a similar role as the diameter of a circular opening, wherein the micro-slits restrict the sound passage thereby providing a relatively small ratio for the acoustic mass over the acoustic resistance. Furthermore, instead of many small openings it is found acoustically comparable to provide the micro-slits with a relatively long total length, wherein the total attenuation can be relatively small, e.g. related to the total open area defined by the slits. At the same time the inventors find that the adaptation of using micro-slits instead of holes, allows more efficient manufacturing of the acoustic filter by means of an injection moulding process at relatively low operating cost. It will be appreciated that, while it is relatively difficult to flow a moulding material through a grid shaped mesh with holes, it is relatively easy to flow the material along defined and relatively wide pathways between the micro-slits.

By providing the foil piece with a relatively small thickness, e.g. less than 0.25 millimetre, preferably less than 0.125 millimetre, an acoustic pathway and hence acoustic resistance of the filter can be further lowered with relatively little influence on the shape of the acoustic transfer function. For example, it is found preferable that the acoustic filter has a ratio of acoustic resistance over acoustic mass larger than ten thousand, larger than fifteen thousand, or even larger than twenty thousand. At the same time by providing a relatively thick support ring attached around a circumference of the foil piece, the filter may be more easy to handle and the foil can be kept tight. For example, the support ring has a ring thickness of more than 0.5, preferably more than 1.5 millimetre. The support ring is thus relatively rigid compared to the foil piece, e.g. having a flexural rigidity that is at least twice as high as that of the foil piece. Advantageously, the foil piece and the support ring can be integrally formed as a single mould piece to provide even further manufacturing benefit. Accordingly, the foil piece and the support ring can be of the same material, e.g. a solidified moulding material, preferably plastic such as Polycarbonate or ABS.

For manufacturability of the mould, a length of an individual one of the micro-slits preferably extends for at least one millimetre along a surface of the foil piece. The micro-slits can be oriented to facilitate the moulding process, e.g. by defining pathways for the moulding material between the slits. The moulding pathways are preferably extending in a direction between a mould entry towards a mould exit. For example the micro-slits are directed towards a centre of the foil piece, wherein an entry nozzle or gate is disposed in an outer ring part and an exit nozzle e.g. air vent is disposed in the inner centre of the foil. To provide sufficient room for the flow of moulding material, it is preferred that the micro-slits are spaced apart on the foil piece by a minimum distance of at least two hundred micrometres. On the other hand it is desirable to provide sufficient coverage for the micro-slits on the surface of the foil to pass the sound. Preferably, the micro-slits define an open area of at least two percent of the foil area.

To improve coverage while maintaining sufficient inter-spacing, adjacent micro-slits can have different lengths. For example, when the micro-slits are radially directed towards a centre of the foil piece, shorter slits can be interposed between longer slits wherein some of the slits extend closer to the centre. An even better coverage may be achieved by arranging the micro-slits in a spiralling (rotation symmetric) pattern around a centre of the foil piece. Accordingly, a spacing between the micro-slits at a centre of the foil piece can be comparable to the spacing at the outer perimeter, e.g. a ratio of the spacings is between 0.5 and 2, preferably between 0.8 and 1.2.

Depending on the application, the foil piece can have a certain maximum surface diameter, e.g. less than ten millimetres, preferably less than five millimetres to fit in an earplug. To facilitate moulding, a central area of the foil piece may be without micro-slits. For example, the central area of the foil piece has a minimum cross-section diameter of at least five hundred micrometres, e.g. 1.5 millimetre. By providing the foil piece with a hydrophobic material, the acoustic filter may have advantageous application to prevent water transmission, even for use under water.

According to one aspect, the present disclosure provides an earplug comprising the acoustic filter as described herein. Typically, the ear plug comprises a plug housing shaped to fit at least partially in an ear canal of a human ear. For example, the plug may comprise a universal or custom plug housing, e.g. otoplastic. To manufacture the earplug, the acoustic filter may be disposed in a filter housing, wherein the filter housing is placed inside a housing cavity of the plug housing. The rigid support ring as describe herein can also directly form the filter housing. The filter housing may be sealed inside the housing cavity. Accordingly, the earplug forms an acoustic seal between an inside of the ear canal and the outside surroundings to receive sound waves from the outside surroundings to provide filtered sound waves by interaction with the acoustic filter.

Another or further aspect of the present disclosure provides a mould for manufacturing the acoustic filter as described herein. It will be appreciated that the mould can be configured to form the micro-slits already during the injection moulding of the acoustic filter. To facilitate removal of the filter after moulding, the mould may comprise two (or more) mould parts configured to fit together with a sealed mould cavity there between. Accordingly, the mould cavity is shaped as a negative of the acoustic filter. For example, the mould comprises a plurality of micro-ridges configured to form the micro-slits. Optionally, the mould comprises a ring shaped cavity configured to form the relatively thick support ring of the acoustic filter.

Either one or both of the at least two mould parts may comprise a respective pattern of ridges. In some embodiments, at least two mould parts are configured to fit together at a specific or variable relative angle of rotation. In this way the overlap of the respective patterns of ridges may be defined and/or varied. For example, the overlap of the respective patterns of ridges determines a width of the resulting micro-slits. By providing an outside visible indicator of a rotation angle, a specific pattern and/or width can be more easily chosen.

Typically, the mould comprises an entry nozzle configured to feed a liquid moulding material into the mould. Preferably, the entry nozzle is at an outer perimeter of the mould cavity, in particular when the outer part comprises a ring shaped cavity having a relatively large width to more easily distribute the material along the ring. To allow air and/or excess liquid moulding material to escape, the mould preferably comprises an air vent. Preferably, the air vent is at a centre of the mould cavity, i.e. at the part that will form the centre of the foil piece. In this way material can distribute from all directions around the ring part and then inward towards the air vent in the centre while filling all parts of the foil between the ridges.

Another or further aspect of the present disclosure provides a method of manufacturing an acoustic filter. The method comprises providing a mould that defines a flat cavity with two parallel surfaces spaced apart to form a foil piece of the acoustic filter. One or both of the parallel surfaces comprises a plurality of ridges to form a respective plurality of micro-slits through the foil piece. The mould is filled with a (liquid) moulding material, which is allowed to harden. Accordingly, the acoustic filter as described herein can be formed.

Preferably, the mould defines a ring shaped cavity surrounding the flat cavity to form a support ring of the acoustic filter. The ring shaped cavity is in fluid connection with the flat cavity. For efficient manufacturing, the method may comprise forming the acoustic filter by integrally moulding the foil piece and the support ring as a single piece. For example the moulding comprises injecting the moulding material into an entry nozzle of the mould at an outer perimeter of the mould cavity and receiving air from an exit nozzle of the mould disposed at a centre of the mould.

Preferably, the mould comprises at least two mould parts configured to fit together with a sealed mould cavity there between to form the acoustic filter. For example the at least two mould parts each comprise a respective pattern of ridges and are configured to fit together at a relative angle with respect to each other for setting a partial overlap of the respective patterns of ridges wherein the partial overlap of the respective patterns of ridges determines a width of the resulting micro-slits. Advantageously, a width of the resulting micro-slits can be less than a width of the respective ridges. Accordingly, because the ridges need not be of microscopic proportions the mould may be relatively easy to manufacture and more durable.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1A:
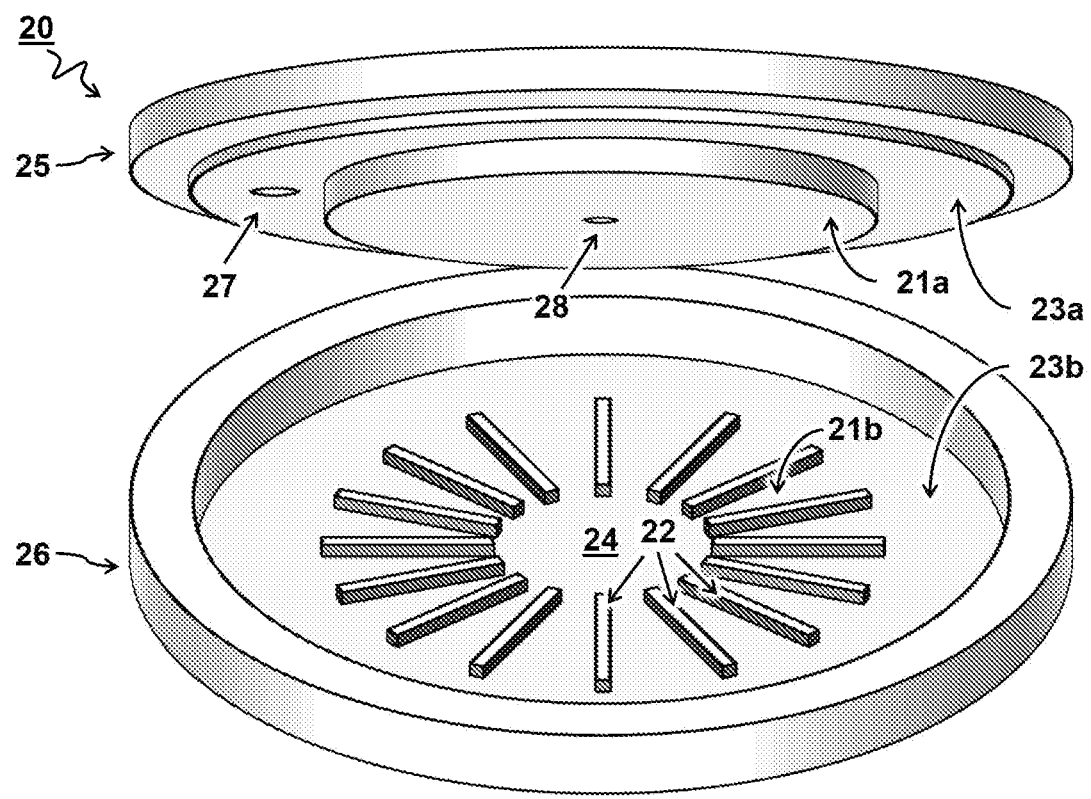
FIG. 1A schematically shows a perspective view of an embodiment of a mould for manufacturing an acoustic filter.

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1B:
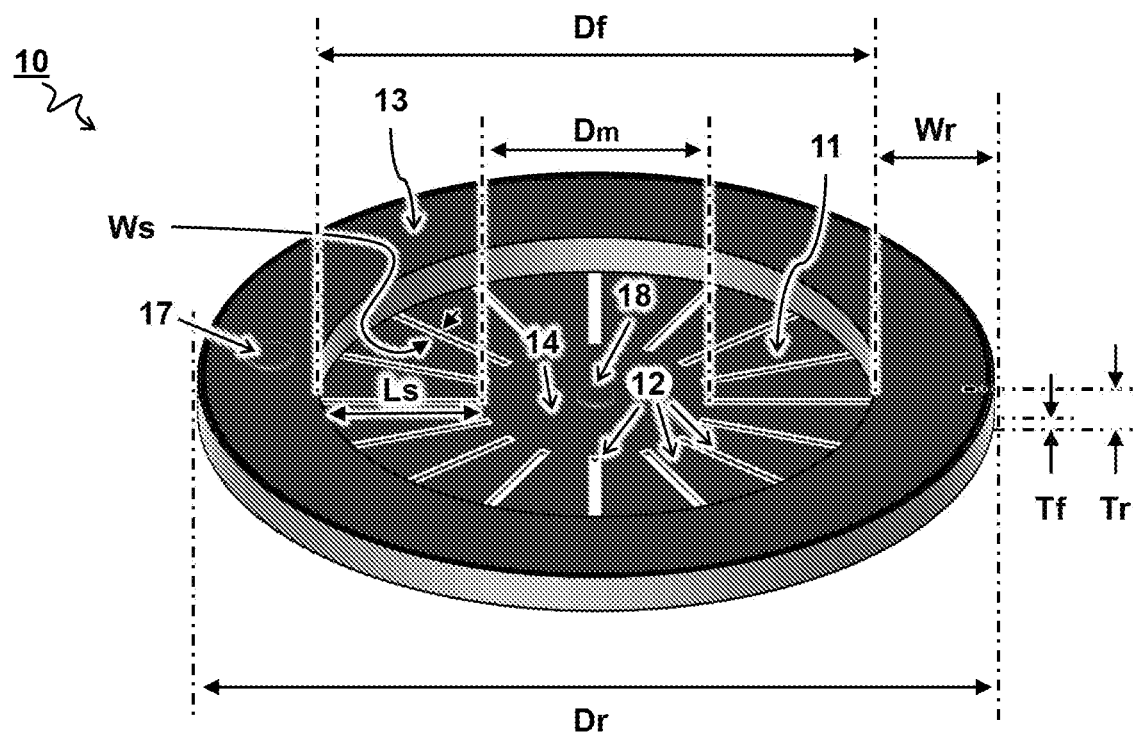
FIG. 1B schematically shows a perspective view of an embodiment of an acoustic filter corresponding to the mould of FIG. 1A.

FIG. 1A schematically shows a perspective view of an embodiment of a mould 20 for manufacturing the acoustic filter 10 shown in FIG. 1B.

With reference to FIG. 1A, the mould 20 generally defines a hollow form or matrix for giving the desired shape to the acoustic filter 10 in a molten or plastic state. In this case, the mould 20 comprises a plurality of micro-ridges 22 configured to form the corresponding micro-slits 12 in the acoustic filter 10. The mould 20 comprises a ring shaped cavity 23a,23b configured to form a relatively thick support ring 13 of the acoustic filter 10. In one embodiment, the mould 20 comprises at least two mould parts 25,26 configured to fit together with a sealed mould cavity there between, wherein the mould cavity is shaped to form the acoustic filter 10. It will be understood that references herein to the length or (negative) shape of the ridges 22 may partly or fully correspond to the length and shape of the resulting micro-slits 12 in the acoustic filter 10, and vice versa. In one embodiment, a mould is produced using milling (machining) or electrical discharge machining down to a feature resolution of forty micrometre.

With reference to FIG. 1B, the acoustic filter 10 comprises a foil piece 11. The foil is a flat thin structure, which can be flexible or rigid. For example, the foil piece 11 has a foil thickness Tf of less than two millimetre, less than one millimetre, or even less than half a millimetre, e.g. hundred micrometre. The foil piece 11 has a plurality of micro-slits 12 configured to act as acoustic channels through the foil piece 11. The acoustic channels may be used for filtering, e.g. selectively passing and/or attenuating, sound waves impinging the foil piece 11. Preferably, the micro-slits 12 have a maximum slit width Ws (across a surface of the foil piece 11) of less than one hundred micrometres.

In one embodiment, the foil piece 11 forms a closed surface except for the openings which act as the acoustic channels. Preferably all the openings acting as acoustic channels have a smallest width or minimum cross-section diameter below a certain threshold, e.g. less than one hundred micrometres. In other words, there are preferably no apertures through the foil piece with a smallest diameter that is more than the threshold, e.g. above one hundred micrometres. Providing only openings having a relatively small minimum cross-section diameter while avoiding apertures with a larger minimum cross-section diameter may facilitate a desired acoustic performance of the filter, e.g. as explained in the introduction.

In the embodiment shown, the openings are formed only by the micro-slits 12 which have a maximum slit width Ws. In other words, the maximum slit width defines the smallest width of the openings. Consequently, the smallest width of any openings through the foil piece is less than the maximum slit width Ws. It will be appreciated that micro-slits have an advantages of manufacturability over e.g. a mesh with holes, especially when the foil piece is manufactured by injection moulding. More particularly, the micro-slits can be formed in the foil piece already during the injection moulding which obviates the need for any further step, e.g. punching.

In one embodiment, a length Ls of an individual one of the micro-slits 12 extends for at least one millimetre along a surface of the foil piece 11. When the individual lengths Ls of all the micro-slits are added up, the micro-slits 12 preferably have a combined slit length (along the surface of the foil piece 11) of at least five millimetre. Alternatively, or in addition, the micro-slits 12 may define an open area of at least five percent, or at least ten percent of the foil area, e.g. between ten and twenty percent. Preferably, the acoustic filter has a ratio of acoustic resistance over acoustic mass larger than ten thousand.

In a preferred embodiment, as shown, the acoustic filter 10 comprises a support ring 13 attached around a circumference of the foil piece 11. Preferably, the support ring has a higher thickness than the foil piece 11. For example, the support ring 13 has a ring thickness Tr of more than half, preferably more than one millimetre. Accordingly, the support ring 13 is relatively rigid compared to the foil piece 11, e.g. having a flexural rigidity that is at least twice as high as that of the foil piece. Preferably, wherein the foil piece 11 and the support ring 13 are integrally formed as a single mould piece. For example, the foil piece 11 and the support ring 13 are of the same material, typically a solidified moulding material such as plastic. The support ring as shown herein is disposed around the foil to support and maintain the shape of the foil in form. It may allow easy and secure placement for example in an earplug.

For some applications, e.g. to fit in an earplug, the foil piece 11 preferably has a maximum surface diameter Df of less than ten millimetres, or even less than five millimetres. In one embodiment, a central area 14 of the foil piece 11 is without micro-slits 12. For example, the central area 14 of the foil piece has a minimum cross-section diameter Dm of at least five hundred micrometres. The central area 14 of the foil piece 11 may correspond to the central area 24 of the mould 20 where in this case the air vent 28 is disposed when the mould parts 25,26 are fitted together.

In some embodiments, the acoustic filter 10 may comprises a first moulding remnant 17 corresponding to the entry channel 27 of the mould 20 used for creating the acoustic filter 10. In the embodiment shown, the first moulding remnant 17 is disposed at an outer support ring 13 surrounding the foil piece 11. In some embodiments, the acoustic filter 10 comprises a second moulding remnant 18 corresponding to an air vent 28 of a mould 20 used for creating the acoustic filter 10. In the embodiment shown, the second moulding remnant 18 is disposed at a centre 14 of the foil piece 11. In other embodiments (not shown), the moulding remnants can be absent, e.g. removed after production.

In one embodiment, a method of manufacturing an acoustic filter 10 comprises filling a mould 20, e.g. as shown, with a moulding material and having it solidify. For example, the mould 20 defines a flat cavity with two parallel surfaces 21a,21b spaced apart to form a foil piece 11 of the acoustic filter 10. One or both of the parallel surfaces may comprise a plurality of ridges 22 to form a respective plurality of micro-slits 12 through the foil piece 11, wherein the micro-slits 12 have a maximum slit width Ws across a surface of the foil piece 11 of less than one hundred micrometres and a combined slit length along the surface of the foil piece 11 of at least ten millimetre. Also other measurements as described herein may be used.

In some embodiments, the mould 20 defines a ring shaped cavity 23a,23b surrounding the flat cavity to form a support ring 13 of the acoustic filter 10. Preferably, the ring shaped cavity is in fluid connection with the flat (foil) cavity. Accordingly, one method comprises forming the acoustic filter 10 by integrally moulding the foil piece 11 and the support ring 13 as a single piece. Typically, the moulding comprises injecting the moulding material into an entry nozzle 27 of the mould 20, e.g. at an outer perimeter of the mould cavity as shown, and receiving air from an air vent 28 of the mould 20, e.g. disposed at a centre of the mould 20 as shown.

In a preferred embodiment, the micro-slits 12 and/or ridges 22 are directed towards a centre 14 of the foil piece 11. For example, the micro-slits 12 and/or ridges 22 are radially directed, as shown.

Figure 2A:
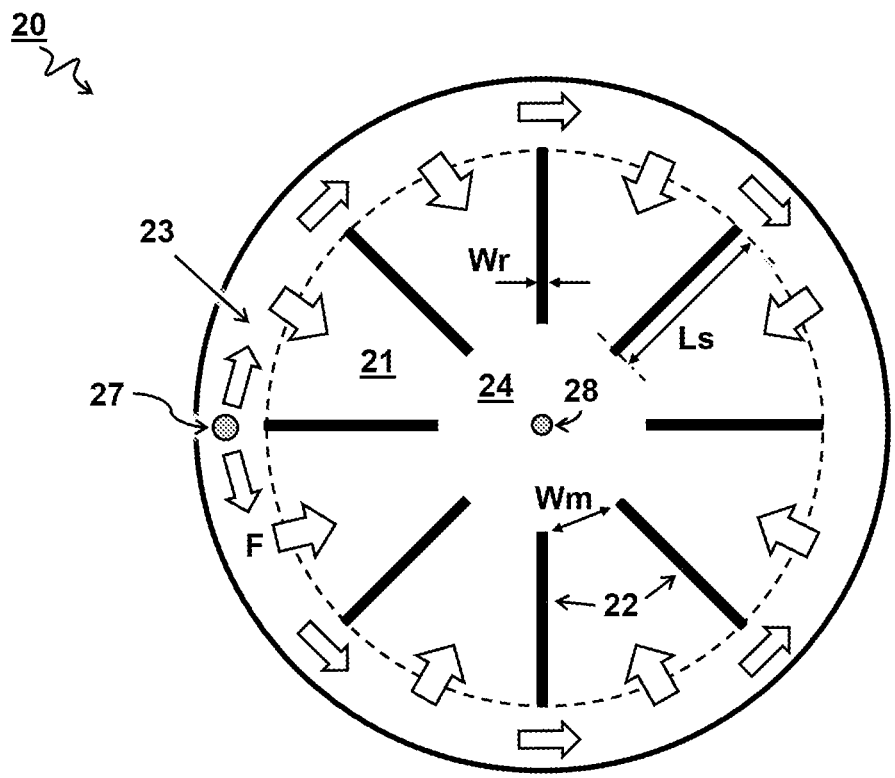
FIGS. 2A, 2B, 3A, 3B, 4A, and 4B schematically show top views of ridge patterns of moulds according to various different embodiments.

FIG. 2A schematically shows a top view of another mould 20 having a radially directed pattern of ridges 22. In one embodiment, the mould 20 comprises an entry nozzle 27 configured to feed a liquid moulding material into the mould 20. Preferably, the entry nozzle 27 is at an outer perimeter of the mould cavity, as shown. In a further embodiment, the mould 20 comprises an exit nozzle 28 configured to allow air and/or excess liquid moulding material to exit the mould 20. Preferably, the exit nozzle 28 is at a centre 24 of the mould cavity, as shown. In the embodiment shown, it is illustrated that a flow F of moulding material entering the nozzle 27 at the periphery may distribute around the outer ring channel 23, e.g. because flow resistance in the channel 23 is relatively low compared to the narrower (thin) compartment 21 which will form the foil piece. When the channel 23 is filled, the moulding material in the channel 23 may be sufficiently pressurized by the continued inflow of material to enter the narrow spacing 21 from all sides towards the central area 24 where the air vent 28 is located.

Also other positions are possible, e.g. the entry nozzle may be disposed at one side of the outer ring. Also multiple entry and/or vent nozzles can be used. For example two or more entry nozzles can be disposed at radial equidistant positions around the outer periphery simultaneously flowing material inward from different directions towards an air vent in the centre.

Figure 2B:
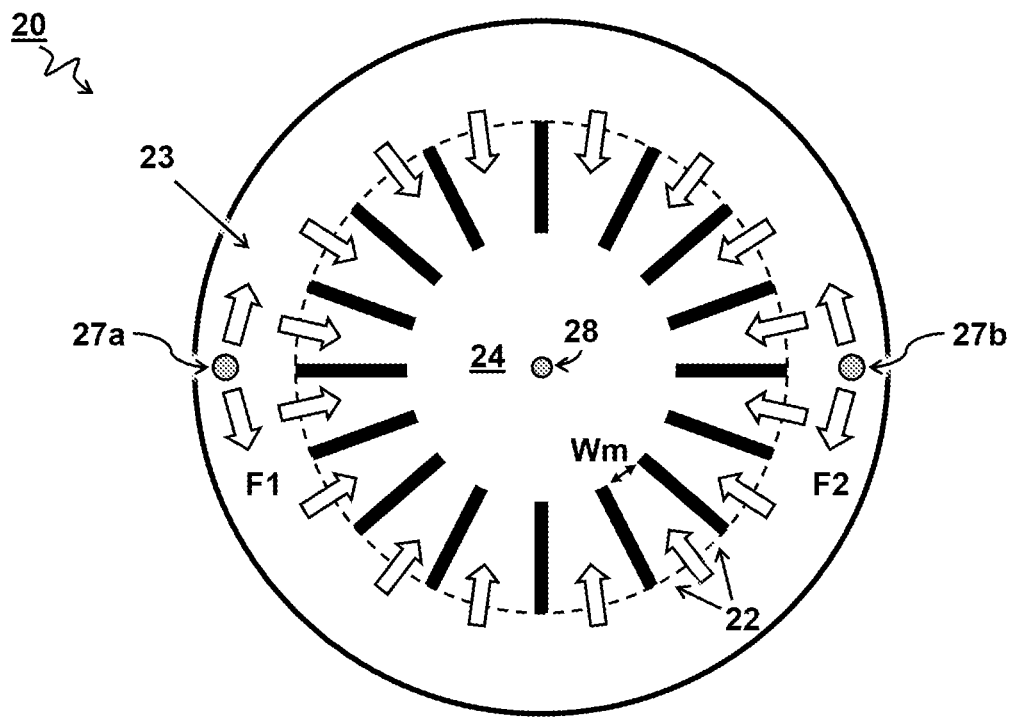

FIG. 2B shows a similar embodiment as FIG. 2A, but having two entry nozzles 27a,27b with respective flow F1,F2. As a further difference, the density of lines 22 is higher in FIG. 2B. Accordingly, the minimum distance Mw between the ridges 22 occurring near the centre 24 is smaller which can cause increased flow resistance for the moulding liquid. Preferably, the micro-slits 12 are spaced apart on the foil piece 11 by a minimum distance Mw of at least two hundred micrometres to allow passage of a flow F of moulding liquid between an entry nozzle 27 and an air vent 28, e.g. at a foil thickness of half a millimetre or less. This may also depend on a thickness of the foil piece to be produced, wherein a thicker foil piece may correspond to a lower flow resistance in the mould and hence allowing less spacing between the ridges 22.

Figure 3A:
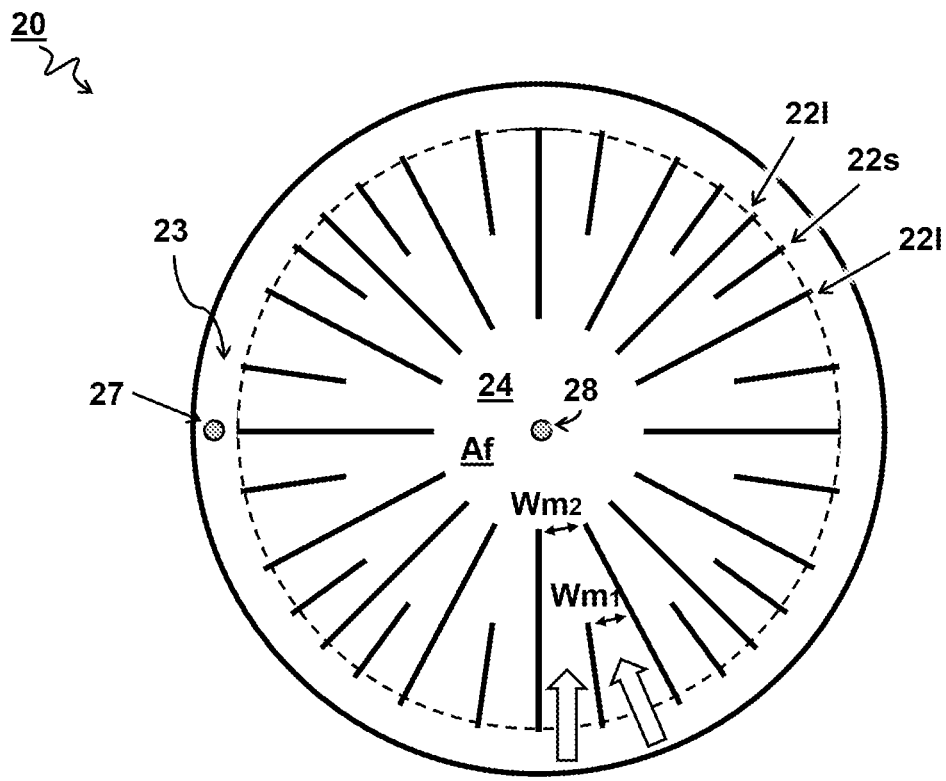

FIG. 3A shows an embodiment wherein adjacent ridges 22l, 22s have different lengths. For example, the ridges 22l extend from an outer perimeter 23 of the mould towards a centre 24 of the mould 20 at a first length and a third ridge 22s, disposed between the ridges 22l, extends from the outer perimeter 23 partly towards the centre 14 of the foil piece at a second length that is smaller than the first length. It will be appreciated that the pattern of this embodiment provides a relatively high density of radially directed lines while keeping a minimum distance Mw1, Mw2.

Figure 3B:
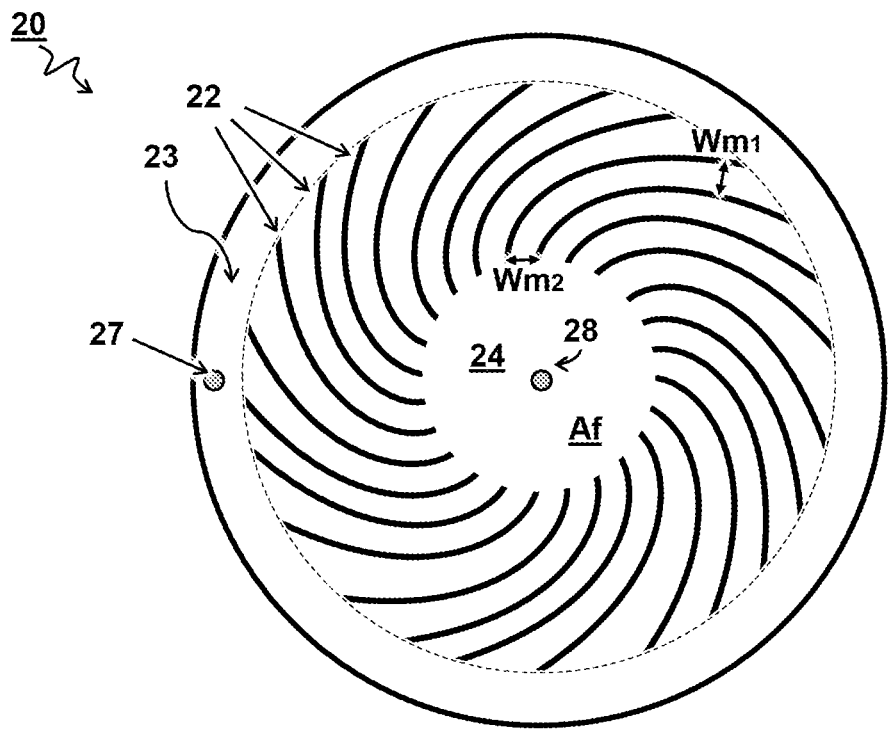

FIG. 3B shows an embodiment wherein ridges 22 are directed in a spiralling pattern around a centre 24 of the foil piece. It will be appreciated that the spiralling pattern can be calculated such that a spacing Mw2 between the ridges 22 at a centre 24 of the mould 20 is similar to a spacing Mw1 between the ridges 22 an outer perimeter 23 of the mould 20. Accordingly, an optimal high density of the corresponding micro-slits 12 in an acoustic filter manufactured with the mould can be achieved while leaving sufficient minimal flow channel width.

Figure 4A:
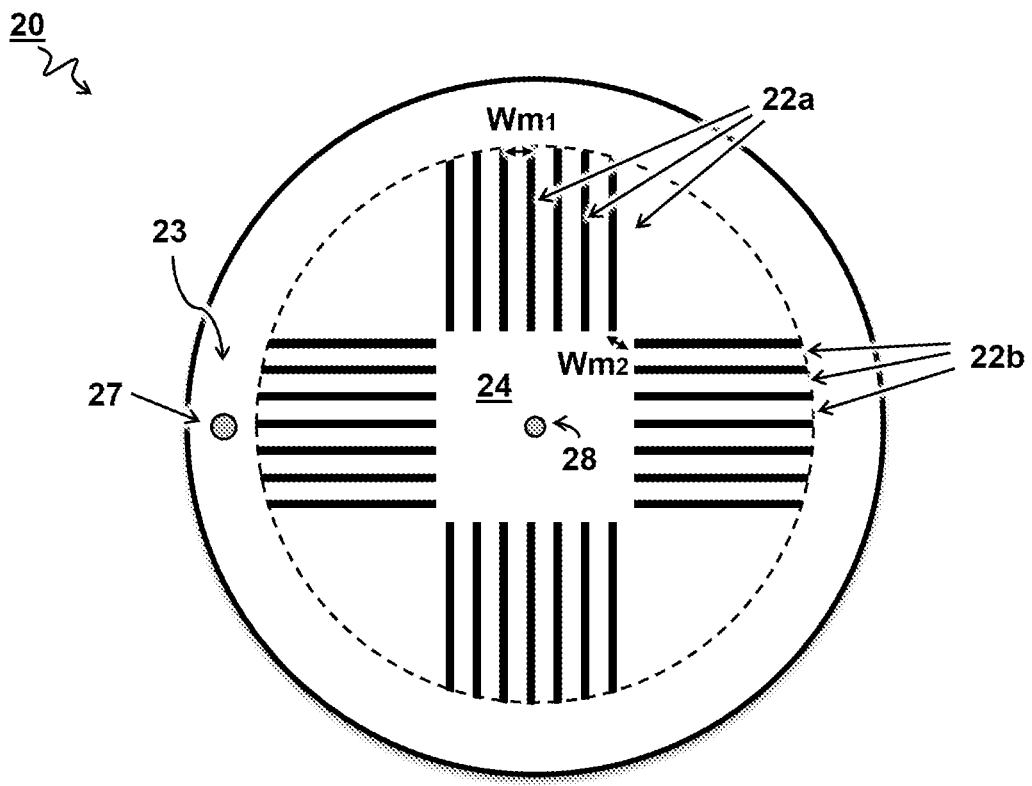
Figure 4B:
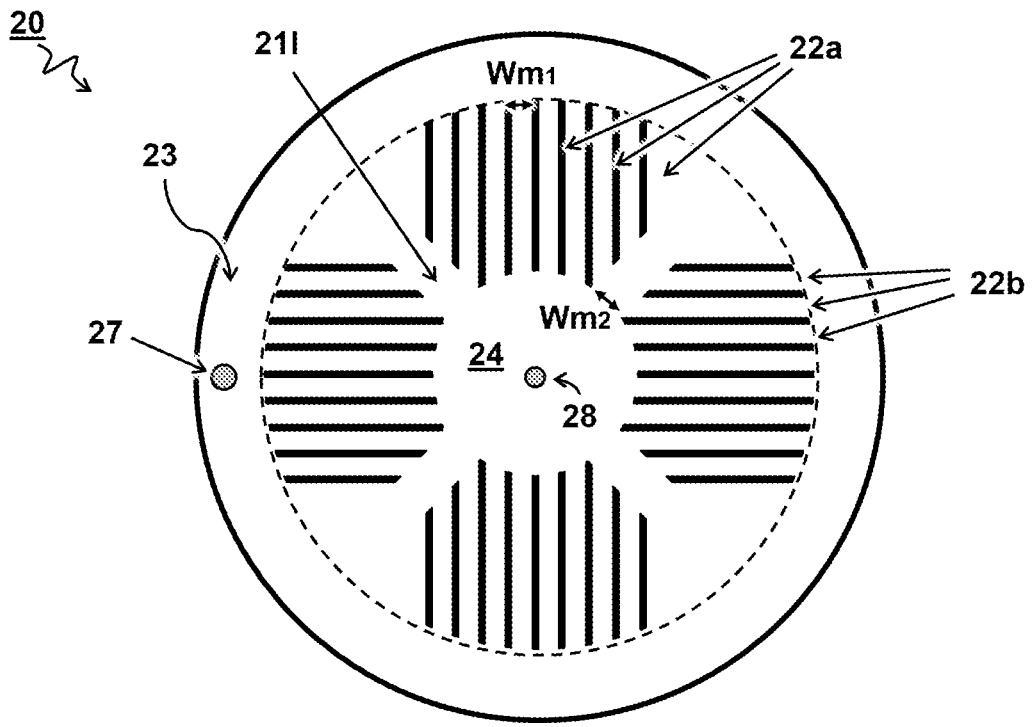

FIG. 4A shows an embodiment wherein ridges 22a,22b are patterned as parallel lines generally directed towards the central area 24 of the mould 20. Advantageously, the distance Mw1 between the ridges can be constant hence providing a predictable flow. Furthermore, the mould 20 may be relatively easy to manufacture. However, the pattern may not fill the entire surface due to the minimum distance Mw2 between the lines of transversely oriented patterns 22a and 22b. FIG. 4B solves this issue by adding lanes 21l between the transverse patterns 22a and 22b. Accordingly, material may flow through the lanes to fill all areas except at the ridges 22a 22b, which can advantageously occupy a relatively larger surface and hence provide a larger open area in the resulting acoustic filter.

Figure 5A:
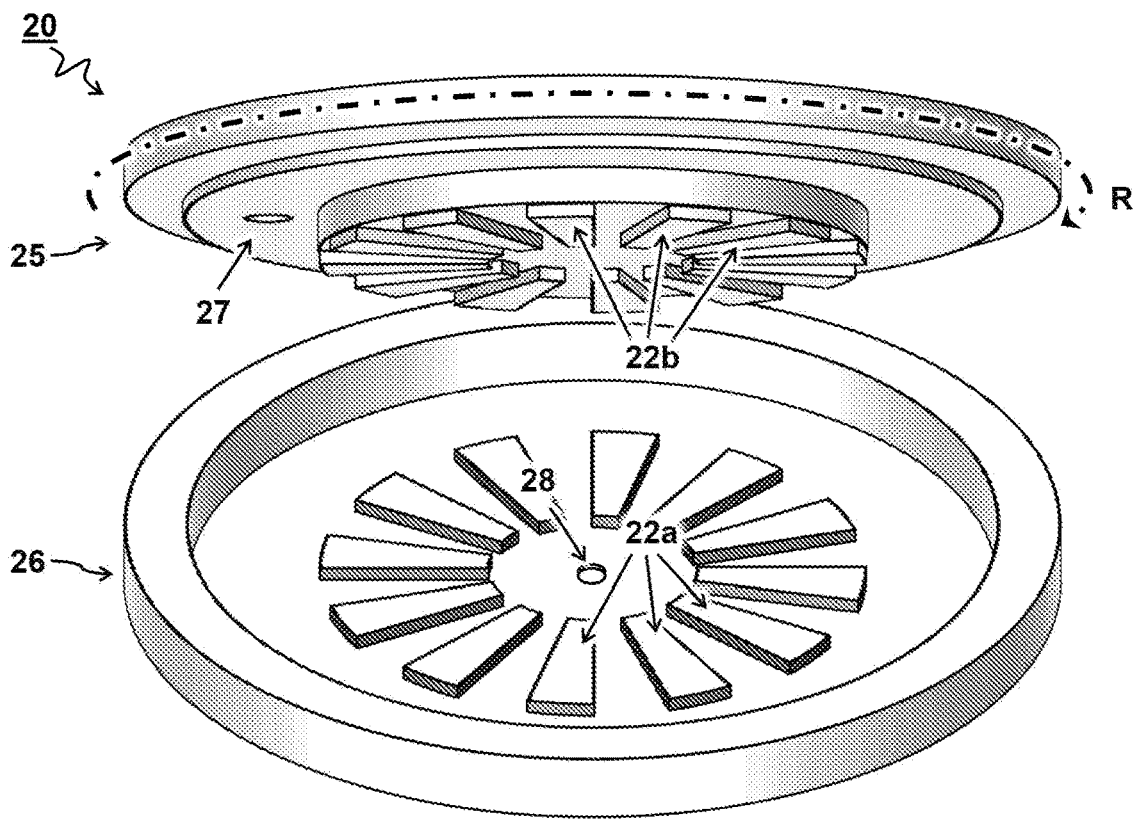
FIG. 5A schematically shows a perspective view of another embodiment of a mould for manufacturing an acoustic filter.
Figure 5B:
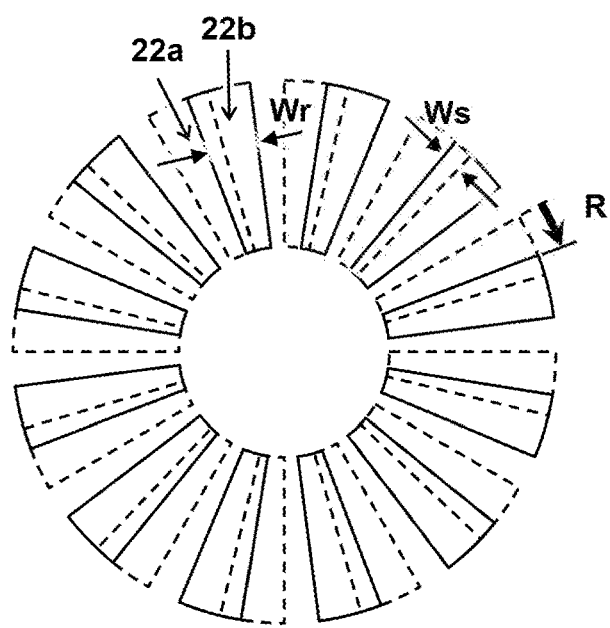
FIG. 5B schematically illustrates a variation in overlap of the ridge patterns in FIG. 5A by relative rotation.

FIG. 5A schematically shows a perspective view of another embodiment of a mould for manufacturing an acoustic filter. In the embodiment, the two mould parts 25,26 each comprise a respective pattern of ridges 22a,22b. For example, the mould parts 25,26 are configured to fit together at different angles of rotation with respect to each other for varying an overlap of the respective patterns of ridges 22a,22b, as illustrated schematically by the top view in FIG. 5B. For example, the overlap of the respective patterns of ridges 22a,22b determines a width Ws of the resulting micro-slits 12. To facilitate setting of the relative rotation, the at least two mould parts 25,26 may comprise an outside visible indicator of a rotation angle there between. It is noted that in this case a width Ws of the resulting micro-slits 12 is less than a width Wr of the of the respective ridges 22a,22b.

According to one method, the mould 20 comprises at least two mould parts 25,26 configured to fit together with a sealed mould cavity there between to form the acoustic filter 10, wherein the at least two mould parts 25,26 each comprise a respective pattern of ridges 22a,22b and are configured to fit together at a relative angle with respect to each other for setting a partial overlap of the respective patterns of ridges 22a,22b wherein the partial overlap of the respective patterns of ridges 22a,22b determines a width Ws of the resulting micro-slits 12.

In an alternative embodiment (not shown), the mould comprises at least two mould parts configured to fit together with a sealed mould cavity there between to form the acoustic filter, wherein the at least two mould parts each comprise a respective pattern of ridges and are configured to cross at a relative angle with respect to each other close to ninety degrees for setting a partial overlap of the respective patterns of ridges wherein the partial overlap of the respective patterns creates rectangular and parallelogram openings.

Figure 6A:
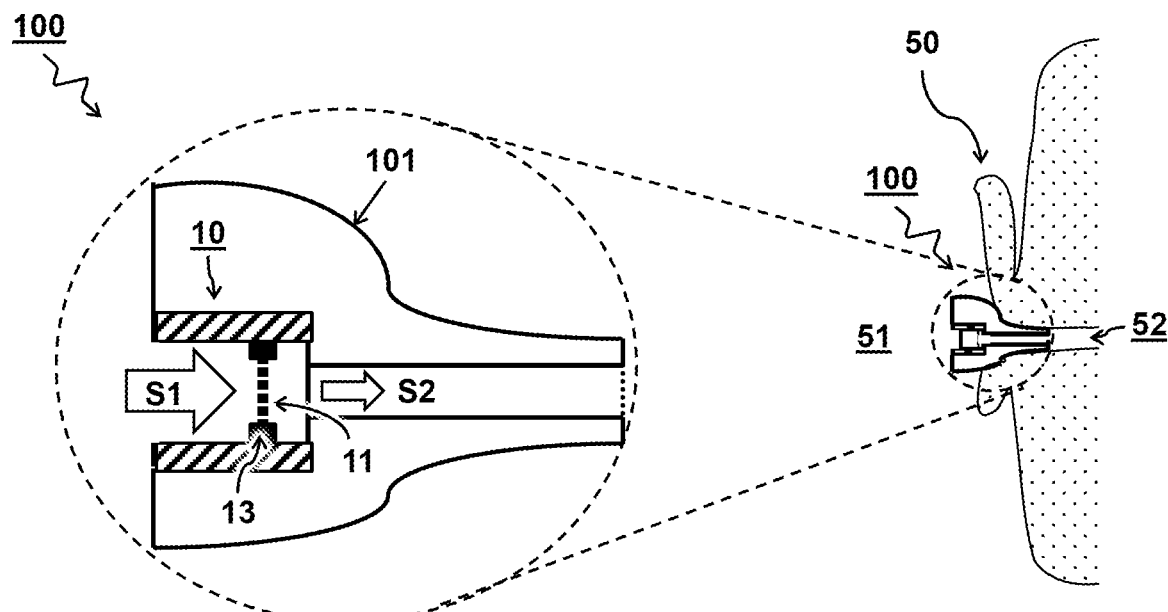
FIG. 6A schematically shows a cross-section view of an acoustic filter in a custom earplug.

FIG. 6A schematically shows a custom earplug 100 comprising the acoustic filter 10 as described herein. In one embodiment, the earplug 100 comprises a plug housing 101 shaped to fit at least partially in an ear canal of human ear 50. The earplug 100 is thus configured to form an acoustic seal between an inside 52 of the ear canal and the outside surroundings 51 to receive sound waves S1 from the outside surroundings 51 to provide filtered sound waves S2 by interaction with the acoustic filter 10.

Figure 6B:
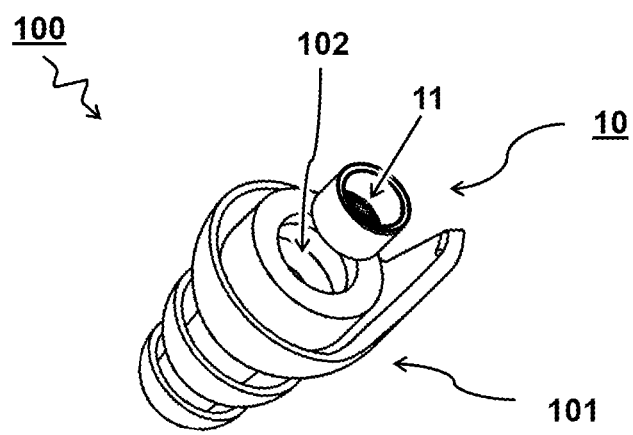
FIG. 6B schematically shows a perspective view an acoustic filter in a universal earplug.

FIG. 6B schematically shows a perspective view of an acoustic filter in a universal earplug. In one embodiment, the acoustic filter 10 is disposed in or integrated with a filter housing. The filter housing may be placed inside a housing cavity 102 of the plug housing 101. In another or further embodiment, the filter housing is acoustically sealed inside the housing cavity 102

Figure 7:
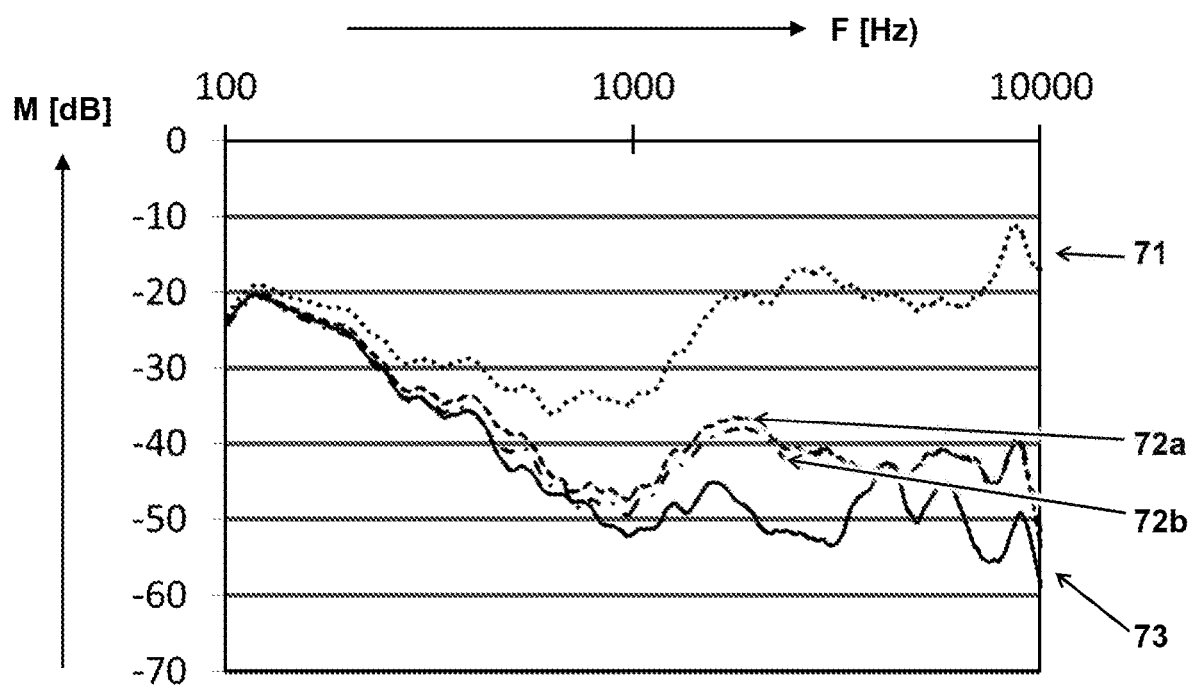
FIG. 7 shows a graph of acoustic transfer functions.

FIG. 7 shows a graph of acoustic transfer functions of the sound magnitude M (in decibel) for different measurements in a frequency range F between 100 and 10000 Hz (100-4000 Hz corresponding to speech). Reference numeral 71 indicates the response for an open artificial ear, i.e. without earplug. Reference numerals 73 indicates the response for an acoustic filter comprising a plate with a 200 µm diameter hole. Reference numerals 72a and 72b indicate the respective responses for a first mesh with 20 µm holes (total diameter of the mesh 1.6 mm) and a second mesh with 6 µm holes (total diameter 4 mm). These graphs illustrate that the mesh provides an improved (flatter) acoustic transfer function, more similar to the open ear than the plate with a single hole.

Figure 8A:
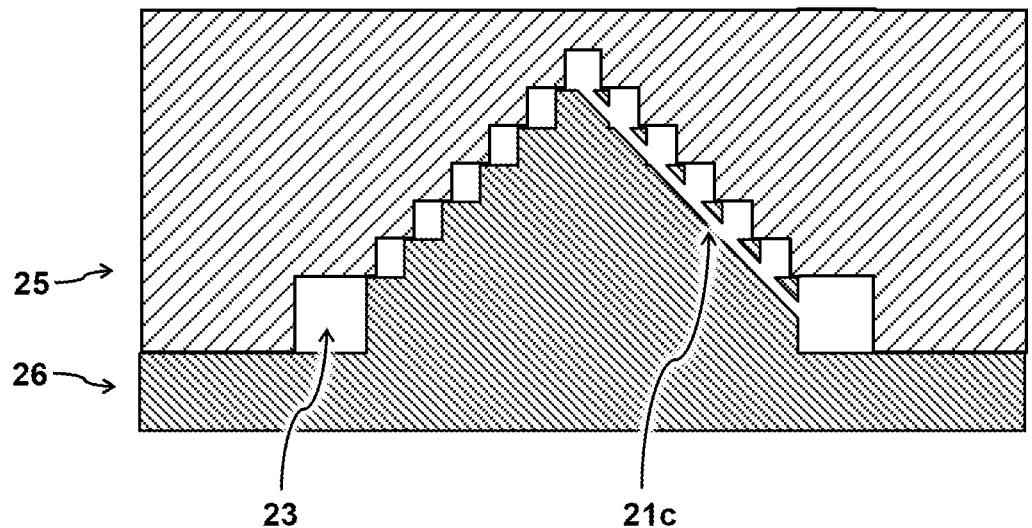
FIGS. 8A, 8B, 9A, and 9B show examples of three dimensional filter structures and corresponding mould pieces.
Figure 8B:
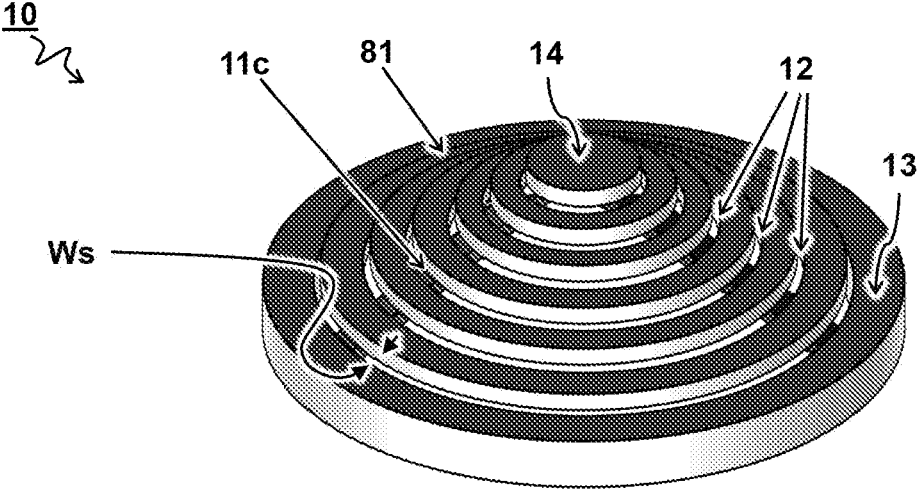

FIGS. 8A and 8B show one embodiment of a mould 20 and corresponding acoustic filter 10, wherein the acoustic filter 10 comprises a three dimensional filter structure 81.

Analogous to the foil piece, as described herein, the filter structure 81 has a plurality of micro-slits 12 configured to act as acoustic channels through the filter structure for filtering sound waves S1 impinging the filter structure 81, wherein the micro-slits 12 have a maximum slit width Ws across a surface of the filter structure of less than one hundred micrometres and a combined slit length along the surface of the filter structure of at least five millimetres. Advantageously, a three dimensional filter structure may provide additional surface area to provide the micro-slits 12 compared to a flat foil piece.

In one embodiment, a support ring 13 is attached around a circumference of the filter structure, wherein the support ring has a higher thickness than the foil piece 11. In another or further embodiment, the filter structure 81 comprises a rim extending at an angle. e.g. transverse to the support ring. In one embodiment, wherein the filter structure 81 comprises a curved surface. In one embodiment, the filter structure 81 comprises a plurality of concentric rings at different heights with respect to the support ring, wherein the micro-slits 12 are formed between the rings. In one embodiment, the rings are connected by one or more cross beam 11c acting as support structure between the rings and/or as pathways (21c) for passing the moulding material between the rings. In one embodiment, the filter structure has a frustoconical or cylindrical shape. The mould 20 has a corresponding (negative) structure, e.g. comprising two pieces 25,26, as illustrated.

Figure 9A:
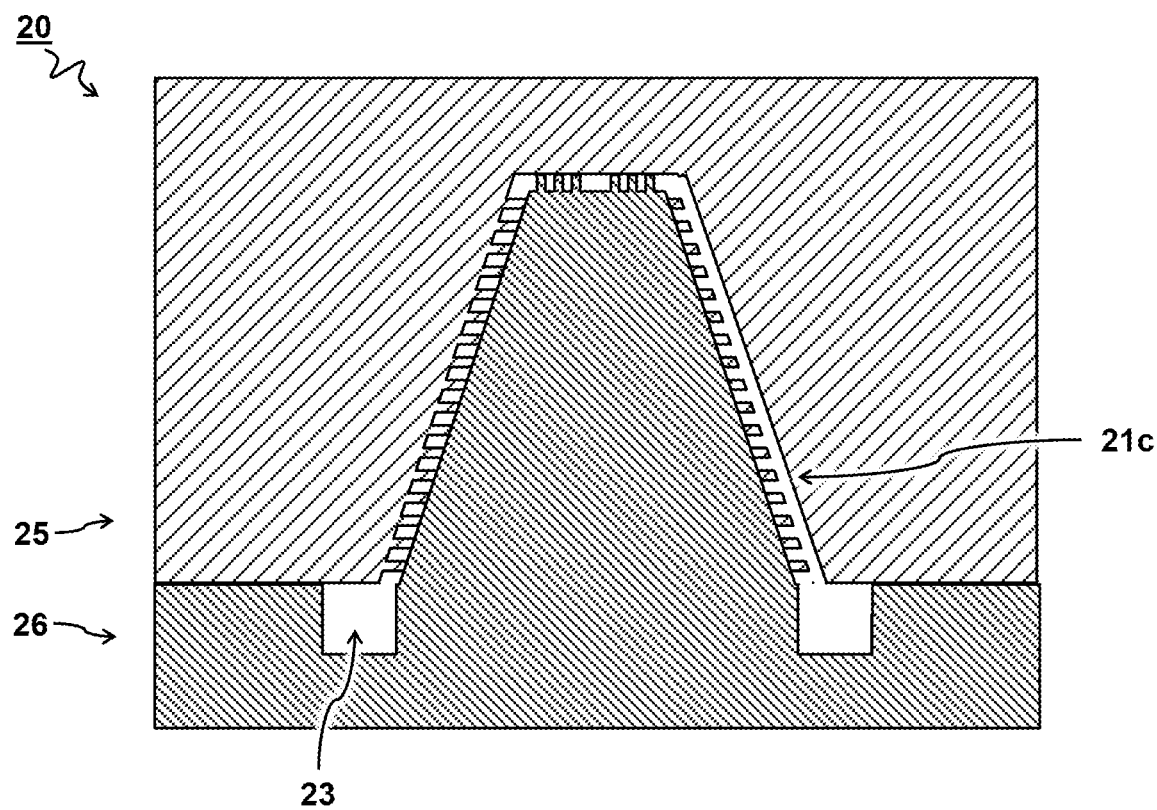
Figure 9B:
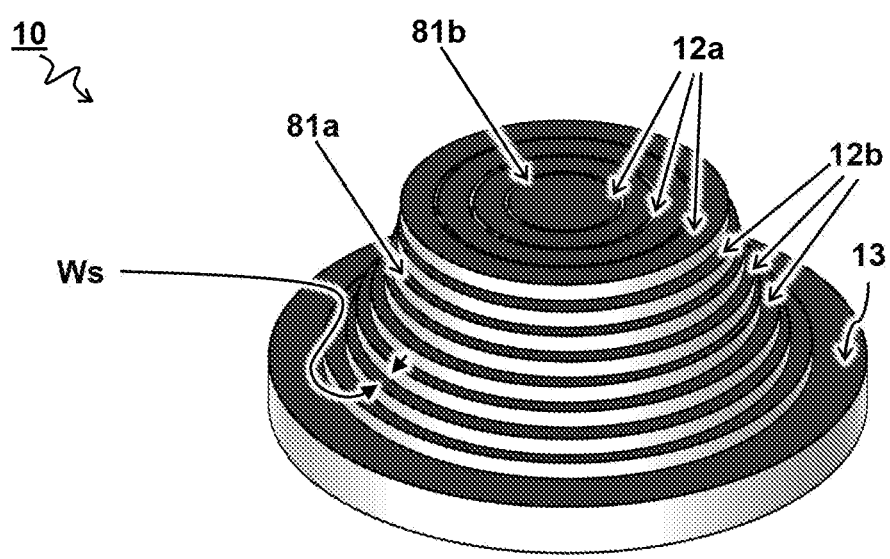

FIGS. 9A and 9B show another embodiment of a mould 20 and corresponding acoustic filter 10, wherein the acoustic filter 10 comprises a three dimensional filter structure 81. In the embodiment, microslits 12a and 12b are formed on different sides of the filter structure 81.

Figure 10A:
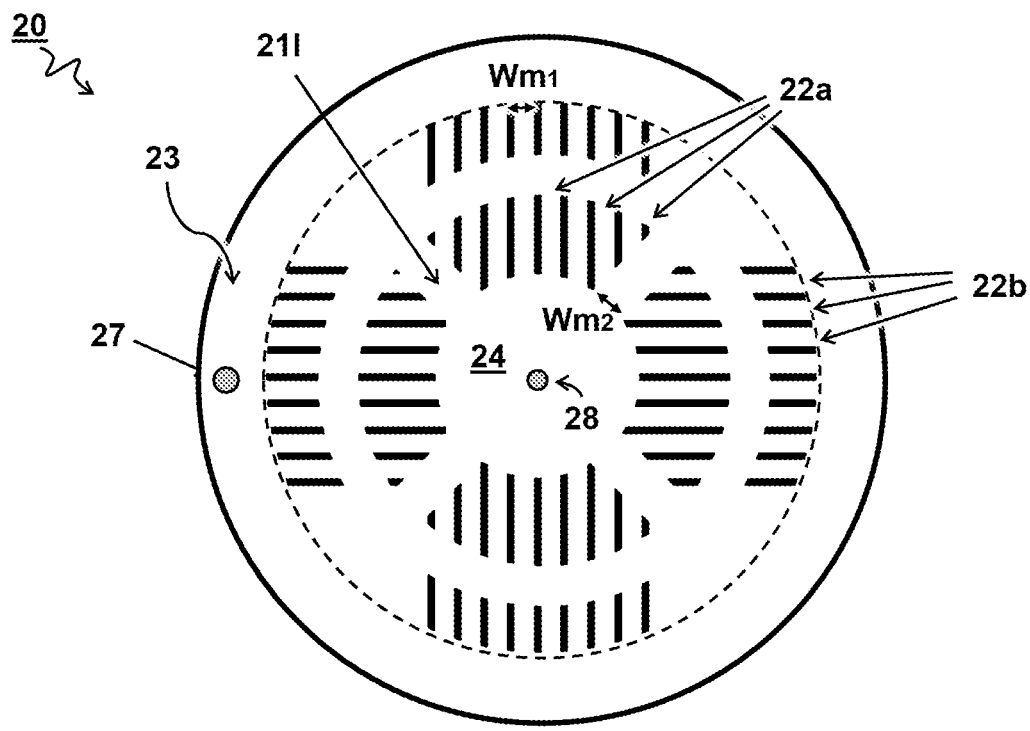
FIGS. 10A and 10B show an embodiment of an earplug comprising multiple channels fitting and corresponding filter.
Figure 10B:
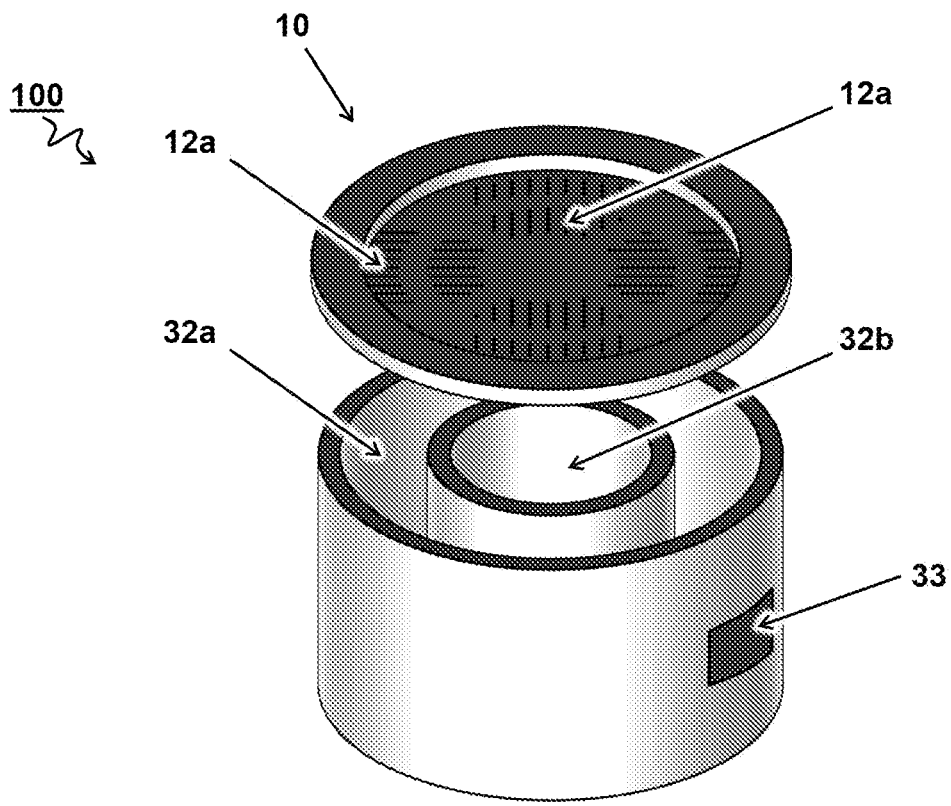

FIGS. 10A and 10B shows an embodiment of an acoustic filter 10 and earplug 100 comprising multiple channels 32a,32. The filter 10 comprises different filter areas with respective microslits 22a, 22b, that fit with the earplug to restrict access to the respective channels 32a,32b. Advantageously, the different channels 32a, 32b may connect to different acoustic inputs or output of the earplug and the respective filter areas 12a, 12b may be configured according to different functions. For example, the first channel 32a may connect to exterior surroundings via an opening 33. For example the second channel 32b may connect to an acoustic generator or microphone.

For the purpose of clarity and a concise description, features are described herein as part of the same or separate embodiments, however, it will be appreciated that the scope of the invention may include embodiments having combinations of all or some of the features described. For example, while embodiments were shown wherein the acoustic filters are round, e.g. to fit in a round earplug, also other shapes are possible, e.g. square or polygonal. For example, aspects relating to the foil, pattern, ring, nozzles etcetera may be combined or omitted into alternative embodiments. It is appreciated that this disclosure offers particular advantages for use in earplugs, and in general can be applied for any acoustic filtering application wherein sound fidelity is important. The aspects as disclosed herein may also provide advantages, even at minimal attenuation e.g. if it is desired to block a canal (e.g. ear) or larger area (e.g. speaker) from water with minimal sound attenuation. For example the foil piece may comprises or be treated with a hydrophobic material to improve moisture repellence. The may also prevent clogging of the filter with moisture. In one embodiment, the filter is used for acoustic filtering, either alone or in combination with other acoustic elements. Alternative applications of the present structures may include controlling a flow rate.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. An acoustic filter comprising an injection moulded foil piece having openings formed as micro-slits configured to act as acoustic channels through the foil piece wherein the openings formed as micro-slits have a maximum slit width across a surface of the foil piece of less than one hundred micrometres, and a combined total slit length of the microslits along the surface of the foil piece of at least five millimetres.

2. The acoustic filter according to claim 1, comprising a support ring attached around a circumference of the foil piece, wherein the support ring has a higher thickness than the foil piece.

3. The acoustic filter according to claim 1, wherein the foil piece has a foil thickness of less than half a millimetre.

4. The acoustic filter according to claim 1, wherein the micro-slits are directed towards a centre of the foil piece.

5. The acoustic filter according to claim 1, wherein the micro-slits are spaced apart on the foil piece by a minimum distance of two hundred micrometres.

6. The acoustic filter according to claim 1, wherein a length of an individual one of the micro-slits extends for at least one millimetre along a surface of the foil piece.

7. The acoustic filter according to claim 1, wherein the foil piece has a maximum surface diameter of less than ten millimetres.

8. An earplug comprising the acoustic filter as claimed in claim 1.

9. The acoustic filter according to claim 2, wherein the foil piece and the support ring are integrally formed as a single mould piece.

10. An acoustic filter comprising a three dimensional filter structure having openings formed as micro-slits configured to act as acoustic channels through the filter structure for filtering sound waves impinging the filter structure, wherein the openings formed as micro-slits have a maximum slit width across a surface of an injection moulded foil piece of less than one hundred micrometres, and a combined total slit length of the micro-slits along the surface of the filter structure of at least five millimetres.

11. A method of manufacturing the acoustic filter according to claim 1 for an earplug, the method comprising filling a mould with a moulding material, wherein the mould defines a flat cavity with two parallel surfaces spaced apart to form the injection moulded foil piece of the acoustic filter, wherein one or both of the parallel surfaces comprises a plurality of ridges to form a respective plurality of micro-slits through foil piece, wherein the micro-slits have the maximum slit width across the surface of the foil piece of less than one hundred micrometres and the combined total slit length along the surface of the foil piece of at least five millimetres.

12. The method according to claim 11, wherein the mould defines a ring shaped cavity surrounding the flat cavity to form a support ring of the acoustic filter, wherein the ring shaped cavity is in fluid connection with the flat cavity, wherein the method comprises forming the acoustic filter by integrally moulding the foil piece and the support ring as a single piece.

13. The method according to claim 11, wherein the mould comprises at least two mould parts configured to fit together with a sealed mould cavity there between to form the acoustic filter, wherein the at least two mould parts each comprise a respective pattern of ridges and are configured to fit together at a relative angle with respect to each other for setting a partial overlap of the respective patterns of ridges—wherein the partial overlap of the respective patterns of ridges determines a width of the resulting micro-slits.

14. The method according to claim 11, wherein the mould comprises an entry nozzle configured to feed a liquid moulding material into the mould, wherein the entry nozzle is at an outer perimeter of the mould cavity; and an exit nozzle configured to allow air to exit the mould, wherein the exit nozzle is at a centre of the mould cavity.

15. An earplug comprising the acoustic filter as claimed in claim 10.

* * * * *